(12) United States Patent
Wester et al.

(10) Patent No.: US 7,794,745 B2
(45) Date of Patent: Sep. 14, 2010

(54) EDIBLE COMPOSITIONS FOR LOWERING CHOLESTEROL

(75) Inventors: Ingmar Wester, Turku (FI); Tapio Palmu, Raisio (FI); Anu Hopia, Helsinki (FI); Pirjo Alho-Lehto, Vanhalinna (FI); Paula Virtanen, Tampere (FI); Anniina Pouru, Raisio (FI)

(73) Assignee: Raisio Nutrition Ltd., Raisio (FI)

( * ) Notice: Subject to any disclaimer, the term of this patent is extended or adjusted under 35 U.S.C. 154(b) by 491 days.

(21) Appl. No.: 10/473,718

(22) PCT Filed: Apr. 12, 2002

(86) PCT No.: PCT/FI02/00315

§ 371 (c)(1),
(2), (4) Date: Mar. 3, 2004

(87) PCT Pub. No.: WO02/082929

PCT Pub. Date: Oct. 24, 2002

(65) Prior Publication Data

US 2004/0131657 A1 Jul. 8, 2004

(30) Foreign Application Priority Data

Apr. 12, 2001 (FI) .................. 20010780

(51) Int. Cl.
- A61K 9/68 (2006.01)
- A23D 7/01 (2006.01)
- A23D 9/013 (2006.01)

(52) U.S. Cl. .................. 424/439; 424/601

(58) Field of Classification Search ........ None
See application file for complete search history.

(56) References Cited

U.S. PATENT DOCUMENTS

| 5,502,045 | A | | 3/1996 | Miettinen et al. |
| 6,117,475 | A | * | 9/2000 | van Amerongen et al. ... 426/601 |
| 6,149,961 | A | * | 11/2000 | Kepplinger et al. ......... 426/553 |
| 6,174,560 | B1 | | 1/2001 | Miettinen et al. |

FOREIGN PATENT DOCUMENTS

| EP | 0 986 962 A1 | 3/2000 |
| WO | WO 98/58554 | 12/1988 |
| WO | WO 93/07167 | 4/1993 |
| WO | WO 94/25042 | 11/1994 |
| WO | WO 95/00158 | 1/1995 |
| WO | WO 95/08342 | 3/1995 |
| WO | WO 99/11144 | 3/1999 |
| WO | WO 99/55351 | 11/1999 |
| WO | WO 00/30663 | 6/2000 |
| WO | WO 01/30359 A1 | 5/2001 |
| WO | WO 01/54686 A2 | 8/2001 |
| WO | WO 01/78522 A2 | 10/2001 |
| WO | WO 01/78529 A2 | 10/2001 |
| WO | WO 01/78534 A2 | 10/2001 |

OTHER PUBLICATIONS

Waiora's Superior Fiber Blend—Product information.*
"Effect of Beta-glucan level in oat fiber extracts on blood lipids in men and women", Bhall, K.M, Journal of the American College of Nutrition, vol. 16, Issue I, 46-51, 1997.*
"Plant sterol and stanol margarines and health", BMJ, 2000:320 861-864 (Mar. 25, 2000).*
Functional Food Fact Sheet: Plant Stanols and Sterols, International Food Information Council, 2009.*
Braaten JT et al., "Oat beta-glucan reduces blood cholesterol concentration in hypercholesterolemic subjects", European Journal of Clinical Nutrition 1994, 48, pp. 465-474.
Patent Abstract of Japan, Publication No. 62-234027, published Oct. 14, 1987.
Nicolosi, et al.,"Nutrient bar reduced cholesterol levels", Food Technology, Abstract,1996, 50(3) 93.
Penteado, et al., "Plant sterols combined with dietary fiber" Abstract of BR 9900399.
Bell et al., "Effect of βGlucan from Oats and Yeast on Serum Lipids", Critical Reviews in Food Science and Nutrition, 39(2): 189-202 (1999).
Leinonen et al., "Rye Bread Decreases Serum Total and LDL Cholesterol in Men with Moderately Elevated Serum Cholesterol", Human Nutrition and Metabolism, pp. 164-170.
Anderson et al., "Long-term cholesterol-lowering effects of psyllium as an adjunct to diet therapy in the treatment of hypercholesterolemia", Am J Clin Nutr 2000; 71: 1433-8.
Ripsin et al., "Oat Products and Lipid Lowering", JAMA, Jun. 24, 1992, vol. 267, No. 24, pp. 3317-3325.
Causey, et al., "Effects of Dietary Inulin on Serum Lipids, Blood Glucose and the Gastrointestinal Environment in Hypercholesterolemic Men", Nutrition Research, vol. 20, No. 2, pp. 191-201, 2000.

* cited by examiner

*Primary Examiner*—Carlos A Azpuru
(74) *Attorney, Agent, or Firm*—Arent Fox LLP

(57) ABSTRACT

The present invention is related to improved compositions for reducing serum total and/or LDL cholesterol levels. The compositions are combinations of dietary fiber and plant sterol. The compositions are used as such or more advantageously in food products and comprise one or several fibers, preferably β-glucan, in combination with one or several plant sterols and/or stanols in their free and/or esterified forms.

56 Claims, No Drawings

EDIBLE COMPOSITIONS FOR LOWERING CHOLESTEROL

CROSS-REFERENCE TO RELATED APPLICATION

This application is a National Stage entry of International Application No. PCT/FI02/00315, filed Apr. 12, 2002, the entire specification claims of which are incorporated herewith by reference.

FIELD OF INVENTION

The present invention relates to the field of nutrition. Especially it concerns improved compositions for oral use suitable for lowering blood serum cholesterol levels and methods for lowering the serum cholesterol levels.

BACKGROUND OF THE INVENTION

According to FAO and WHO dietary fibres are constituents of substances of both animal and plant origin that are resistant to hydrolysis by human alimentary enzymes. Another generally accepted definition is that dietary fibres are the remnants of edible plant cell polysaccharides, lignin and other associated substances resistant to digestion by the alimentary enzymes of humans. According to these two definitions fibres can be obtained from grains, legumes, fruits, vegetables, algae or other plants or microbial or animal origin either as extracts, concentrates, bran or specific part of plant material containing a sufficient amount of active fibre ingredient.

The dietary fibres consist of insoluble and soluble substances. The insoluble polysaccharides include mainly cellulose and hemicellulose. The soluble polysaccharides include β-glucans, plant extrudates (gums), mucilages, legume seed gums, seaweed polysaccharides, bacterial polysaccharides, resistant starch or non-polysaccharide lignins. The cholesterol lowering effects have mainly been associated to soluble fibres because of their viscosity behaviour but also insoluble fibres may affect the serum cholesterol levels.

β-glucan and especially β-glucan from oat is known to have cholesterol lowering effect, which has been acknowledged also by health authorities. FDA has approved a health claim on the cholesterol lowering effect for oat products containing at least 0.75 grams of oat β-glucan per serving. The amount of β-glucan needed for an effect on cholesterol levels is 3 grams per day (recommended daily dosage) divided to 3 or 4 servings per day.

FDA has also approved a healthy claim for soluble fibre of psyllium containing at least 1.7 grams of soluble fibre per serving and the recommended daily intake of soluble fibre is 7 grams.

Consumption of diets with high β-glucan content has shown to lower the total and low density lipoprotein (LDL) cholesterol level by 8-12% (Ripsin et al., J. Am. Med. Assoc. 1992 (267) 3317-3325, Braaten et al., Eur. J. Clin. Nutr. 1994 (48) 465-474)

There is also evidence of the cholesterol lowering effect of the soluble fibres of psyllium (Anderson et al., Am. J. Clin. Nutr. 2000 (71) 1433-8) inulin (Causey et al., Nutrition Research 2000, 20(2), 191-201) and rye (Leinonen et al., J. Nutr. 2000 (130) 164-170) as well as microbial β-glucans (Bell et al., Crit. Rew. in Food Sci. and Nutr. 1999, 39(2) 189-202).

It is known that plant sterols (i.e. sterols and stanols) as well as esters thereof have serum cholesterol level lowering effects. Stanol fatty acid esters and the cholesterol lowering effects thereof are disclosed in U.S. Pat. Nos. 5,502,045 and 6,174,560 as well as a suitable method for their preparation.

Dietary intake of 2 to 3 g/day of plant sterols is reported to lower the serum LDL levels in man by on average 10%-14% thus reducing the risk of coronary heart disease (CHD). Plant sterols inhibit the absorption of biliary and dietary cholesterol from the intestinal lumen.

The current literature and especially FDA's conclusion to allow the health claim for plant sterols has increased the interest of the food industry in supplementing foods with plant sterols. Indeed, many such food items have recently been introduced into the market. It is assumed that new plant sterol containing foods will appear into the market rapidly.

This active launching of new plant sterol containing foods has raised a concern that a part of the population may have higher daily intake of plant sterols than needed to obtain an optimal cholesterol lowering effect. Short-term high intake of plant sterols has not been shown to be harmful. However, there are no data on possible long-term side effects of ingestion of high daily amounts of plant sterols. Furthermore, currently there is not a clear understanding on the biological impact of the increased serum level and thus higher systemic availability of plant sterols caused by increased intake from sterol-enriched foods, especially of foods enriched with unsaturated plant sterols (here called sterols). Therefore, there is a need of food products having a high enough reducing effect on total and/or LDL serum cholesterol levels and containing somewhat elevated levels of plant sterols, in which products the cholesterol reducing effect has still been enhanced by other means.

SUMMARY OF THE INVENTION

The present invention relates to improved compositions suitable for reducing serum total and/or LDL cholesterol levels in man. The compositions comprise combinations of dietary fibres and plant sterols. The compositions can be used as such or as pharmaceuticals or nutraceuticals or most advantageously in food products. The compositions comprise one or several fibres used in combination with one or several plant sterols (sterols and/or stanols) in their free and/or esterified forms. A typical example of such an improved composition is a mixture of plant sterols and a soluble fibre, such as oat β-glucan, advantageously used in foods. The food products contain at least two of the active ingredients in sufficient amounts to provide a reduction in serum total and/or LDL cholesterol levels. In a preferred embodiment of this invention such reduction in serum total and/or LDL cholesterol levels is obtained by oral ingestion of a low daily dose of plant sterols and a soluble fibre such as β-glucan. This can be provided for the consumer in an easy way by including both plant sterol and β-glucan in the same food product.

Since β-glucan increases the viscosity of the content of the intestine, it was expected that β-glucan would inhibit or substantially decrease the cholesterol-lowering effect of plant sterols. However, it was surprisingly found that the two active components work synergistically in reducing the blood serum total and/or LDL cholesterol levels. In the tests performed it was shown that plant sterols in combination with dietary fibre (β-glucan) had a reducing effect on the cholesterol levels that was greater than the possibly expected additive effect.

The present invention also discloses a method for minimising the daily intake of plant sterols in man still achieving a similar cholesterol lowering effect as obtained with recommended daily intake of plant sterols from commercial plant sterol enriched products. This is especially important as the daily amount of plant sterols needed for obtaining a reduction in serum total and LDL cholesterol can be reduced, thus preventing potential over-consumption of plant sterols. Furthermore, the commercial availability of plant sterols is limited. By the use of the compositions according to the present invention the plant sterols supply can be more effectively utilised with the aim of reducing the risk of coronary heart disease (CHD) in individuals and in the population. In addition commercial crude plant sterols are expensive due to their limited availability. The present invention provides a way of obtaining similar serum cholesterol reductions as obtained with plant sterols alone, but with a markedly lower daily intake of plant sterols. As dietary fibres are cheaper than plant sterols the present invention also provides a way of obtaining an optimal cholesterol lowering effect more cost effectively.

The present invention also provides a method to improve the sensory properties such as structure and mouthfeel of food products with high fibre content. Dietary fibre, especially soluble fibre is a food component with known and recognised cholesterol lowering effect. However, the cholesterol lowering effect is achieved with remarkably high fibre content, which very often cause organoleptic problems for foods deteriorating structure and mouthfeel of foods such as breads and cakes. The present invention combining dietary fibre and plant sterols in cholesterol lowering products such as foods provides a way to obtain nutritionally a cholesterol lowering effect by lower fibre content in foods. Furthermore, the daily amount needed of dietary fibres to obtain reductions in total and/or LDL cholesterol levels cause in many subjects gastrointestinal discomfort. The present invention provides means for reducing such gastrointestinal discomfort with at least as efficient cholesterol lowering effect.

In practising the present invention ingredients of special interest are plant sterol and β-glucan. Plant sterol and psyllium (the soluble fibres of psyllium) are another preferred combination as well as plant sterol and inulin or some other combination of above ingredients such as β-glucan, inulin and plant sterol.

DETAILED DESCRIPTION OF THE INVENTION

In one aspect of the present invention there is provided a food product for lowering serum total and/or LDL cholesterol levels comprising at least one basic nutritional ingredient, dietary fibre and a plant sterol, said dietary fibre and said plant sterol both being present in a higher amount than the one naturally occurring in the basic nutritional ingredient(s).

Dietary fibre is in this specification meant to include all edible fibres that have a lowering effect on the serum total and/or LDL cholesterol levels. Said dietary fibre is preferably a soluble fibre, such as β-glucan. By β-glucan is here meant intact β-glucans. An especially preferred dietary fibre is oat β-glucan. By soluble fibre is here meant soluble fibres that lower the serum total and/or LDL cholesterol levels. Other suitable fibres than β-glucan are inulin, the soluble fibres of psyllium (preferably used together with the insoluble fibres of psyllium), glucomannans, galactomannans, gum arabicum and guar gum. The term inulin is here meant to include all fructo oligosaccharides that can be measured by the AOAC standard method 997.08. Use of mixtures of any of these fibres, such as e.g. inulin and β-glucan is also preferred.

By the term plant sterol is in this specification meant both sterols and saturated sterols i.e. stanols either in their free form or esterified with e.g. fatty acids (2-24 carbon atoms, saturated, monounsaturated or polyunsaturated, including also special fatty acids such as conjugated fatty acids (e.g. CLA) and EPA and DHA), hydroxybenzoic acids or hydroxycinnamic acids (ferrulic or coumaric acids) or other organic acids such as e.g. di- or tricarboxylic acids and/or hydroxy acids.

In this specification the sterols include 4-desmethyl sterols, 4-monomethyl sterols, and 4,4-dimethyl sterols (triterpene alcohols) and the stanols include 4-desmetyl stanols, 4-monomethyl stanols and 4,4-dimethyl stanols. Typical 4-desmethyl sterols are sitosterol, campesterol, stigmasterol, brassicasterol, 22-dehydrobrassicasterol, Δ5-avenasterol. Typical 4,4-dimethyl sterols are cycloartenol, 24-metylenecycloartanol and cyclobranol. Typical stanols are sitostanol, campestanol and their 24-epimers, cycloartanol and saturated forms obtainable e.g. by saturation of triterpene alcohols (cycloartenol, 24-metylenecycloartanol and cyclobranol).

By the term plant sterol is in this specification further meant all possible natural blends of 4-desmethyl sterols and stanols, 4-monomethyl sterols and stanols, 4,4-dimethyl sterols and stanols and mixtures of natural blends as well as any individual 4-desmethyl sterol, 4-monomethyl sterol or 4,4-dimethyl sterol or their corresponding saturated forms.

The amounts of plant sterol are in this specification calculated as plant sterol equivalents i.e. as the amount of free plant sterol.

Preferably the plant sterol is esterified and most preferably it is a plant sterol fatty acid ester. The fatty acid ester is technically very suitable to incorporate in a wide range of different products and it is especially preferred as it produces a fibre-rich food product with good organoleptic properties.

Preferably the plant sterol is a stanol because its absorption is neglectable and the use of stanol is therefore safer. Also the cholesterol lowering effect seems to be stronger with stanols.

The food product of the present invention can be in the form of various food compositions, including fresh bakery products (fresh bread, cakes, muffins, waffles etc.), dry bakery products (crispbread, biscuits, crackers etc.), cereal products (breakfast cereals, fibre and sterol enriched flours, mueslis, cereal based and muesli bars, such bars possibly containing chocolate, pasta products, snacks etc.), bran products (granulated and/or toasted bran products, flavoured and/or sterol coated bran products and bran-bran mixes etc.), beverages (alcoholic or non-alcoholic drinks, juices and juice-type mixed drinks, and dietary supplement and meal replacement drinks etc. as well as concentrates or premixes for beverages (whereby the plant sterol and β-glucan content is calculated for the ready to use-form), dairy (milk based products, like milkshake, yoghurt, ice cream, desserts, cheese, spreads etc.) and/or non-dairy products (milk-type cereal and/or vegetable products and fermented cereal and/or vegetable products such as drinkables, desserts, yoghurt-, ice cream-, cheese-type products etc.). An especially preferred food product is a cereal milk product, preferably oat milk product or a product based on that, such as ice cream, ready mixes (for baking e.g. breads, cakes, muffins, waffles, pizzas, pancakes; or for cooking e.g. soups, sauces, desserts, puddings) to be used in preparing or manufacturing of foods meat products (sausages, meat-balls, cold cuts etc.)

vegetable oil based products (spreads, salad oils, mayonnaise etc.)

In a second aspect of the present invention there is provided a pharmaceutical or nutraceutical composition for lowering serum total and/or LDL cholesterol levels comprising at least one compounding agent, a dietary fibre and a plant sterol, the weight ratio of said plant sterol to said dietary fibre being 1 to 2-5. The compounding agent can be any pharmaceutically acceptable diluent or excipient or coating agent. The composition can be in any suitable form e.g. tablets, granules, powder, capsules or dispersions.

The present invention also relates to the use of a composition comprising dietary fibre and a plant sterol in a combined amount effective for lowering serum total and/or LDL cholesterol levels for preparing a medicament for oral administration for lowering serum total and/or LDL cholesterol levels.

The products and compositions of the present invention contain at least two active ingredients in sufficient amounts to provide a reduction in serum total and/or LDL cholesterol levels. The daily intake of the compositions as such or when used in foods is such that it supplies a daily intake of plant sterols (calculated as sterol equivalents) of 0.4-5 g, preferably 0.5-2.5 g, more preferably 0.8-2 g and most preferably 0.8-1.6 g and a daily intake of soluble fibre of 1-10 g, preferably 2-5 g and more preferably 2-3 g.

In a further aspect of the invention there is provided a method for lowering serum total and/or LDL cholesterol levels of a subject, comprising orally administering to the subject a composition comprising dietary fibre and a plant sterol in a combined amount effective for lowering serum total and/or LDL cholesterol levels.

A preferred embodiment of the present invention provides a way of obtaining reductions in serum total and/or LDL cholesterol levels with a combined use of elevated but low daily doses of plant sterols and $\beta$-glucan.

The present invention also makes it possible to reduce the daily intake of plant sterols in man still achieving similar cholesterol lowering effects as obtained with generally recommended daily intake of plant sterols (1.6-3 g) which can be achieved e.g. by consuming plant sterol-enriched commercial products.

According to the present invention it is also possible to lower the fibre content of food products with enhanced fibre content especially purposed for cholesterol lowering, thus improving e.g. the technological properties of such foods, their structure and organoleptic properties.

Further, the present invention provides a method to reduce or prevent the development of atherosclerosis in humans by dietary means including plant sterol and dietary fibre.

In a preferred embodiment of this invention the reduction in serum total and LDL cholesterol is obtained by oral ingestion of a low daily dose of plant sterols and a soluble fibre such as $\beta$-glucan and/or the soluble fibres of psyllium.

In another preferred embodiment of this invention the reduction in serum total and LDL cholesterol is obtained by oral ingestion of a low daily dose of plant sterols and a soluble fibre such as $\beta$-glucan and/or inulin.

The present invention is especially directed to an optimal daily intake of plant sterol and soluble fibre to achieve a nutritionally significant serum total and/or LDL cholesterol lowering effect in form of a food product as part of the daily diet.

When $\beta$-glucan is combined with plant sterols the optimal daily intake of plant sterol is less than 1.5 g/day (calculated as sterol equivalents), more preferably about 1 g plant sterol/day in combination with 2-5 g, more preferably about 2.5 g soluble fibre preferably $\beta$-glucan/day. The invention is also directed to a food or drink containing at least 10% of the optimal daily intake/portion of the compositions.

It was surprisingly also realised that the weight ratio of plant sterol (calculated as sterol equivalents) to $\beta$-glucan at a range of 1 to 2-5 (i.e. 0.2-0.5) gave unexpected good synergistic effects. Also from a technical point of view this ratio seems to be surprisingly suitable for manufacturing a wide range of food products. The structure also seems to be soft and the food product tasty i.e. the organoleptic properties are improved in many foods where the ratio is in the mentioned range.

According to the present invention the dietary fibre can be incorporated into the food products or compositions as fibre concentrate or as flour or fibre containing sufficient amount of active ingredient. Mostly preferred are $\beta$-glucan enriched flour fractions like fibre-rich oat bran, enriched oat flake, enriched oat flour or any kind of $\beta$-glucan concentrates, extracts or other isolates.

The main advantages of the present invention obtained by combining the intake of active ingredients into a food product containing a sufficient amount of $\beta$-glucan and plant sterols are:

synergistic total and/or LDL cholesterol lowering effect of $\beta$-glucan and plant sterols enhanced serum cholesterol lowering effect compared to plant sterols alone lower daily intake of plant sterols is needed compared to plant sterols alone to achieve the same cholesterol reducing effect lower fibre content of high fibre foods for improved technological properties, structure and organoleptic properties lowering the risk for coronary heart disease.

The two active ingredients of the present invention are incorporated into the daily diet in the form of food products containing a sufficient amount of the ingredients. The content of the two ingredients in food products is typically from 0.05 to 12.5 g of plant sterols, preferably from 0.05 to 2 g, and from 0.1 to 25 g of soluble fibre, preferably from 0.1 to 5 g in 100 g food product.

In the following some typical food products of the present invention and the preferred amounts of the $\beta$-glucan and plant sterol included therein are set forth. The percentages are calculated on the basis of the weight of the food product.

Beverage comprising $\beta$-glucan in an amount of 0.1-5%, preferably 0.5-1%, and plant sterol in an amount of 0.05-4%, preferably 0.2-1.5%.

Fresh bakery product comprising $\beta$-glucan in an amount of 0.9-16%, preferably 2.4-10%, and more preferably 3-5%, and plant sterol in an amount of 0.3-8%, preferably 0.8-5%, and more preferably 1-4%.

Dry bakery product comprising $\beta$-glucan in an amount of 1.0-20%, preferably 3.2-15% and more preferably 4.4-10%, and plant sterol in an amount of 0.5-10%, preferably 1.6-7.5% and more preferably 2.2-5%.

Cereal product comprising $\beta$-glucan in an amount of 0.8-20%, preferably 1.6-16%, more preferably 2-10%, and plant sterol in an amount of 0.4-10%, preferably 0.8-8%, more preferably 1-5%.

Bran product comprising $\beta$-glucan in an amount of 4%-25%, preferably 6-20%, and plant sterol in an amount of 0.8-12.5%, preferably 1.2-10%.

Dairy or non-dairy product (e.g. fermented cereal product) comprising $\beta$-glucan in an amount of 0.1-20%, preferably 0.8-8%, more preferably 0.8-5%, and plant sterol in an amount of 0.05-10%, preferably 0.4-4%, more preferably 0.4-2.5%.

Vegetable oil based product comprising $\beta$-glucan in an amount of 0.6-16%, preferably 2.6-10%, more preferably 2.6-5%, and plant sterol in an amount of 0.2-8%, preferably 1.3-5%, more preferably 1.3-2.5%.

Meat product comprising β-glucan in an amount of 0.1-16%, preferably 0.2-5%, and plant sterol in an amount of 0.05-8%, preferably 0.1-2.5%.

Ready mix comprising β-glucan in an amount of 0.1-20%, preferably 1-10%, and plant sterol in an amount of 0.05-10%, preferably 0.5-5%.

For plant sterols the intake is preferably from 0.4 to 5 g/day, more preferably from 0.5 to 2.5 g/day and most preferably about 1 g plant sterol/day divided into 0.5-5 servings as free or in esterified form. For soluble fibre the intake is preferably from 1 to 10 g/day, more preferably from 2 to 5 g/day and most preferably about 2.5 g soluble fibre/day in 1-5 servings of food items. In food items the level of active ingredient is preferably 50% of the daily need/serving (from 10% to 200% per serving).

The combination of the two active ingredients (soluble fibre, especially β-glucan, and plant sterol) provides enhanced cholesterol lowering effect as compared to the two active ingredients alone.

According to one preferred embodiment food products according to the invention contain in addition to plant sterol and β-glucan also inulin. Typically these food products contain from 0.05 to 12.5 g of plant sterols, preferably from 0.05 to 2 g, and from 0.1 to 25 g of soluble fibre, preferably from 0.3 to 15 g in 100 g food product, wherein the soluble fibre comprises from 0.05 to 24.95 g of β-glucan, preferably from 0.1 to 5 g, and from 0.05 to 24.95 g of inulin, preferably from 0.2 to 10 g in 100 g food product.

In food products with high water content (e.g. more than 30%, preferably more than 50%, even more preferably more than 75%) (e.g. beverages, desserts, dairy and non-dairy food products) a high amount of β-glucan is not very desirable because of the high viscosity obtained when using most of the currently existing commercial β-glucan rich concentrates. It was noticed that by adding inulin in addition to β-glucan and plant sterol very attractive food products could be prepared also outside the preferred plant sterol to β-glucan weight ratio (1 to 2-5). Without any adverse effect on the synergistic cholesterol lowering features the amount of β-glucan could be reduced e.g. by adding at least the same amount of inulin to the food product. Typically the amount of inulin to soluble fibre (β-glucan and inulin) is 0.3-0.95:1, more preferably 0.6-0.9:1 in these products.

The advantages of adding a sufficient amount of inulin or replacing a part of the β-glucan with inulin in a product that contains β-glucan and plant sterols compared to a product that contains only plant sterols and β-glucan are e.g.
- enhanced serum cholesterol lowering effect compared to plant sterols and β-glucan alone
- enhanced prebiotic properties
- improvement of the technological structure of certain products such as ice cream, pasta products, bakery products and desserts
- improvement of the sensory properties of certain products such as ice cream, pasta products, bakery products, desserts, beverages and drinkables.

In the following some typical food products of the present invention and the preferred amounts of β-glucan, inulin and plant sterol included therein are set forth. The percentages are calculated on the basis of the weight of the food product.

Beverage comprising β-glucan in an amount of 0.1-2%, preferably 0.3-1%, inulin in an amount of 0.2-10%, preferably 0.5-8%, and plant sterol in an amount of 0.05-4%, preferably 0.2-1.5%.

Dairy and/or non-dairy product (e.g. fermented cereal product) comprising β-glucan in an amount of 0.1-5%, preferably 0.5-3%, more preferably 0.8-2.5%, inulin in an amount of 0.1-15%, preferably 0.2-10% and more preferably 0.5-6%, and plant sterol in an amount of 0.05-10%, preferably 0.4-4%, more preferably 0.4-2.5%.

Fresh bakery product comprising β-glucan in an amount of 0.9-16%, preferably 2.4-10%, and more preferably 3-5%, inulin in an amount of 0.5-10%, preferably 1-6% and more preferably 1-3%, and plant sterol in an amount of 0.3-8%, preferably 0.8-5%, and more preferably 1-4%.

An especially preferred embodiment is an oat milk product or oat milk based product, such as oat milk based ice cream. These type of food product may typically comprise β-glucan in an amount of 0.1-5%, preferably 0.2-3.5% and more preferably 0.5-2.5%, inulin in an amount of 0.5-10%, preferably 1-6% and more preferably 1-3%, and plant sterol in an amount of 0.05-8%, preferably 0.5-5% and more preferably 0.8-2%. A preferred combination of the active ingredients in these type of food products comprises 1-2,5% β-glucan, 0.5-10% inulin and 0.1-5% plant sterol. Besides all other in this specification already mentioned beneficial features, the taste of an oat milk product comprising the three active ingredients is surprisingly excellent and brings forward a soft taste of oat by weakening the strong taste effect of β-glucan.

The oat milk product may naturally contain some amounts of β-glucan, e.g. 0.1-0.5%. Also these natural β-glucan containing oat, milk products are meant to be included in this preferred embodiment of the present invention.

The improved efficacy of a food product containing a combination of oat β-glucan and plant sterols was shown in a controlled study. Plant sterols were incorporated into the diet by providing 0.5 g stanol (administered as fatty acid ester) in a food item twice a day. Oat fibre containing 1.25 g β-glucan was incorporated into a food item consumed twice a day. A food product according to the invention containing both 0.5 g stanol (administered as fatty acid ester) and 1.25 g β-glucan was consumed twice a day by a third group of subjects.

The serum total and LDL cholesterol lowering effect of the food product containing the composition according to the invention was markedly higher than that of foods containing either of the active components alone and even higher than the possibly expected additive effect. Thus, it was concluded that plant sterol esters and β-glucan have a synergistic effect in lowering serum total and LDL cholesterol.

When incorporated into the diet the combined effect of β-glucan and plant sterols is beneficial as follows:
- to achieve enhanced cholesterol lowering effect of plant sterols when incorporated simultaneously into the diet with oat β-glucan. The combination of plant sterols and oat β-glucan is most preferably incorporated into foods designed for part of healthy diet.
- to decrease the dietary intake of plant sterols when combined and incorporated simultaneously with oat β-glucan into the daily diet with special aim to lower serum total and LDL cholesterol.
- to lower the risk of CHD by means of lowering serum cholesterol levels.

It is evident from prior art that plant sterols, especially stanol fatty acid esters more effectively reduce serum total and LDL cholesterol as compared to dietary fibres such as β-glucan. The cholesterol-lowering effect of β-glucan is not as strong especially when used as part of recommended diets. It was, however, surprisingly found that a low daily dose of β-glucan in combination with stanol ester had a synergistic cholesterol lowering effect. Surprisingly similar reduction as seen with optimal daily intake of stanol ester alone was obtained. Thus, advantageously the daily intake of plant sterols can be decreased by combining the beneficial effect of plant sterols and other cholesterol lowering dietary components to achieve similar cholesterol lowering effect as obtained with optimal daily intake (2-3 g/day) of plant sterols. This approach advantageously reduces the daily intake of plant sterols, leading to a more balanced use of plant sterols. The synergistic effect is especially profound at daily intakes of at most 2 g plant sterol.

An especially preferred embodiment of the invention is the daily oral use of 0.8-1.6 g plant sterols (calculated as sterol equivalent), preferably 0.8-1.2 g plant sterol in combination with at least 1.6 g β-glucan, preferably 2-5 g, and most preferably 2-3 g β-glucan. Preferably the plant sterol used is a plant sterol fatty acid ester and even more preferred it is a plant sterol fatty acid ester containing a substantial amount of stanol fatty acid ester e.g. at least 30% stanol fatty acid ester.

In the following the invention will be further illustrated by means of examples. In this specification the percentages are % by weight unless otherwise specified.

Example 1

A muffin or cake containing oat fibre (containing β-glucan) and sterol ester in effective amounts

| Ingredients | | Dietary fibre (g) | β-glucan (g) |
|---|---|---|---|
| 223 g | wheat flour | 6.7 | |
| 255 g | fibre enriched oat bran | 55 | 30 |
| 380 g | sugar | | |
| 370 g | vegetable fat | | |
| 25 g | sterol fatty acid ester (15 g sterol equivalents) | | |
| 92 g | egg powder | | |
| 24 g | whey powder | | |
| 16 g | baking powder | | |
| 8.5 g | lecithin | | |
| 1.5 g | salt and flavorings | | |
| 370 g | water | | |

The cake and the muffins were prepared in a conventional way.

The plant sterol content was 0.94% and the β-glucan content 1.89% of the ready product. The weight ratio of plant sterol to β-glucan was 0.50.

Example 2

Oat fibre and plant sterol are combined in an oat milk drink or dessert with efficient amount of both active ingredients. Some drinks and desserts are prepared by adding inulin and possibly reducing the amount of β-glucan to obtain suitable products with synergistic cholesterol lowering effect.

Ingredients: Water, soluble fibre enriched oat concentrate, vegetable oil, plant sterol fatty acid ester, emulsifier, stabilising agent, and possibly inulin. The following compositions were made:

| | 1 drink | 2 dessert | 3 dessert | 4 | 5 dessert |
|---|---|---|---|---|---|
| Plant sterol content | 0.25 | 0.8 | 1.2 | 1.6 | 1.2 g/100 g |
| β-glucan content | 0.50 | 2.3 | 2.5 | 3.6 | 2.0 g/100 g |
| inulin content | 0 | 0 | 0 | 0 | 4.0 g/100 g |
| sterol: (β-glucan + inulin) | 0.50 | 0.35 | 0.48 | 0.44 | 0.20 |
| inulin: (β-glucan + inulin) | | | | | 0.67 |

| | 6 drink | 7 drink | 8 drink | 9 drink | 10 drink |
|---|---|---|---|---|---|
| Plant sterol content | 0.25 | 0.8 | 1.2 | 1.6 | 1.0 g/100 g |
| β-glucan content | 0.50 | 0.5 | 0.5 | 0.5 | 0.5 g/100 g |
| inulin content | 0.50 | 1.8 | 2.0 | 3.1 | 4.5 g/100 g |
| sterol: (β-glucan + inulin) | 0.25 | 0.35 | 0.48 | 0.44 | 0.20 |
| inulin: (β-glucan + inulin) | 0.5 | 0.78 | 0.80 | 0.86 | 0.90 |

Example 3

Oat Bran Bread

| Ingredients | | Dietary fibre (g) | β-glucan (g) |
|---|---|---|---|
| 570 g | fibre-rich oat bran | 124.3 | 50.7 |
| 240 g | oat bran concentrate | 105.6 | 52.8 |
| 790 g | wheat flour | 23.7 | |
| 30 g | salt | | |
| 50 g | stanol fatty acid ester | | |
| 120 g | gluten | | |
| 30 g | baking powder | | |
| 1750 g | water | | |

The stanol content of the ready bread was 0.96% and the β-glucan content was 3.3%. The weight ratio of plant sterol to β-glucan was 0.29.

Example 4

Fibre and Plant Sterol are Combined in a Bread Pre-Mix

| Ingredients | | Dietary fibre (g) | β-glucan (g) |
|---|---|---|---|
| 455 g | oat flake | 50 | 18.6 |
| 450 g | oat bran concentrate | 140 | 104 |
| 250 g | malted rye flake | 35 | 5 |
| 95 g | sourdough, dried | 8 | |
| 100 g | rye flour (whole grain) | 14 | 2 |
| 95 g | stanol fatty acid ester (fatty acid composition as in rapeseed oil) | | |

The pre-mix is then used for making bread by mixing the following ingredients with the pre-mix in a conventional manner:

| | | Dietary fibre(g) |
|---|---|---|
| 3500 g | water | |
| 1165 g | wheat flour | 38 |
| 60 g | salt | |
| 60 g | sugar | |
| 40 g | baking powder | |
| 75 g | sirup | |

The ready bread contained 1.0% stanol and 2.3% β-glucan (the ratio of plant sterol to β-glucan was 0.43).

Example 5

Energy Bar Containing β-Glucan and Plant Sterol

| Ingredients | Dietary fibre (g) | β-glucan (g) |
|---|---|---|
| 200 g oat flake | 22 | 8 |
| 95 g fibre-rich oat bran | 19 | 9.5 |
| 97 g wheat flake | 10 | |
| 100 g malted oat kernel | 11 | 4 |
| 140 g sugar sirup | | |
| 110 g brown sugar | | |
| 40 g concentrated apple juice | | |
| 20 g apple | | |
| 60 g raisin | | |
| 105 g vegetable fat | | |
| 5 g salt | | |
| 15 g stanol fatty acid ester (9 g sterol equivalents) | | |
| 10 g flavourings | | |
| 3 g lecithin | | |

The bars contain 0.9% stanol and 2.2% β-glucan. The weight ratio between stanol and β-glucan is 0.42.

Example 6

Biscuit Containing β-Glucan and Plant Sterol

| Ingredients | |
|---|---|
| 100 g | margarine containing stanol fatty acid ester (8% free stanol i.e. sterol equivalents) |
| 170 g | sugar |
| 90 g | fibre-rich oat bran containing 8 g β-glucan |
| 40 g | oat bran concentrate containing 8.8 g β-glucan |
| 2 g | baking powder |
| 1 g | vanillin sugar |
| 120 g | egg |

The plant sterol content was 1.5% of the dough (1.8% per ready product), the β-glucan content 3.2% of the dough (3.9% per ready product) and the weight ratio of plant sterol to β-glucan was 0.46.

Example 7

Muesli Mixture Containing β-Glucan and Stanol Fatty Acid Ester

| | Ingredients | Dietary fibre (g) | β-glucan (g) |
|---|---|---|---|
| 430 g | oat flake | 47 | 17.2 |
| 95 g | fibre-rich oat bran | 19 | 9 |
| 50 g | rye flake | 7 | 1 |
| 50 g | wheat germ | 7 | |
| 100 g | brown sugar | | |
| 70 g | sugar syrup | | |
| 5 g | salt | | |
| 30 g | apple flake | 3.5 | |
| 50 g | raisin | 4.8 | |
| 30 g | hazel nut | 1.8 | |
| 60 g | vegetable fat | | |
| 20 g | stanol fatty acid ester | | | stanol content 1.2% (as sterol equivalents)
β-glucan content 3.6%
Weight ratio of stanol to β-glucan 0.33

Example 8

Fermented Yoghurt-Like Cereal Product Containing β-Glucan and Plant Sterol

| Ingredients | |
|---|---|
| 59.4 g | water |
| 7 g | fibre enriched oat bran (containing 0.7 g β-glucan) |
| 30 g | berry jam (containing sugar, cowberry, blueberry, strawberry, raspberry, pectin, flavor) |
| 0.58 g | plant sterol fatty acid ester |
| 3 g | lecithin |

The mixture of water and oat bran was fermented using Lactobacillus and a bifidobacteria culture. The sterol was mixed with the lecithin and all ingredients were worked together.

The product contained plant sterol 0.35% and β-glucan 0.7%. The weight ratio between plant sterol and β-glucan was 0.5.

Example 9

Fermented Dairy Product Containing Soluble Fibre (Inulin and β-Glucan) and Plant Sterol

| Ingredients | |
|---|---|
| 31 g | milk |
| 31 g | oat milk |
| 45 g | fibre enriched oat bran (containing 3 g β-glucan) |
| 30 g | berry jam (containing sugar, cowberry, blueberry, strawberry, raspberry, pectin, flavor) |
| 1.5 g | inulin |
| 1.6 g | sterol fatty acid ester (0.96 g sterol equivalents) |
| 10 g | lecithin |
| | bacteria culture (lactobacillus acidophilus, bifidobacterium etc.) |

The sterol content of the product was 0.64%, the β-glucan content 2.0% and the soluble fibre (inulin and β-glucan) 3.0%. The weight ratio between sterol and β-glucan was 0.32 and between sterol and soluble fibre 0.21.

Example 10

Fruit Drink Containing Soluble Fibre (β-Glucan and Inulin) and Plant Sterol

| Ingredients | |
|---|---|
| 200 g | fruit juice concentrate (banana, pine apple, orange, grape, apricot, lemon, passion fruit, guava, mango) |
| 5 g | fructose |
| 1 g | inulin |
| 10 g | fibre enriched oat bran (12% β-glucan) |
| 0.9 g | plant sterol fatty acid ester (= 0.54 g sterol equivalents) |
| 5 g | lecithin |
| 2 g | β-glucan concentrate (25% β-glucan) |
| 1.5 g | calcium lactate |
| 775 g | water |

The product contained 0.054% plant sterol and 0.17% β-glucan, and the soluble fibre content was 0.27%. The ratio of plant sterol to β-glucan was 1:3.1 (i.e. 0.32) and between plant sterol and soluble fibre (β-glucan and inulin) 1:5 (i.e. 0.2).

Example 11

Vanilla Ice-Cream-Type Food Product Containing Stanol Ester, β-Glucan and Inulin

| Ingredients | |
|---|---|
| 64.5 g | oat milk (containing 0.5 g β-glucan) |
| 8.0 g | sugar |
| 6.5 g | vegetable oil |
| 6.0 g | inulin |
| 4.0 g | starch syrup |
| 1.7 g | plant stanol fatty acid ester (=1 g plant stanol equivalents) |
| 6.0 g | β-glucan concentrate (25% β-glucan) |
| 3.0 g | emulgators (synthetic emulgators and lecithin) |
| 0.3 g | aromas (vanilin) |

The product contained 1% plant stanol and 2% β-glucan, and the soluble fibre content was 8%. The ratio of plant sterol to β-glucan was 1:2 (i.e. 0.50) and between plant sterol and soluble fibre (β-glucan and inulin) 1:8 (i.e. 0.125) and inulin to soluble fibre 1:1.33 (i.e. 0.75).

Example 12

Fruit Muesli Containing Stanol Ester and β-Glucan

| Ingredients | |
|---|---|
| 6 g | oat flake |
| 24 g | oat bran concentrate |
| 2.5 g | plant stanol ester (=1.5 g plant stanol equivalents) |
| 6.6 g | oat bran |
| 6.0 g | sugar |
| 3.0 g | rice crispy |
| 3.5 g | vegetable oil |
| 4.5 g | syrup |
| 0.3 g | salt |
| 3.6 g | fruit mixture |

The product contained 2.5% plant stanol and 8.3% β-glucan. The ratio of plant stanol to β-glucan was 1:3.3 (i.e. 0.30).

Example 13

Fermented Yoghurt-Like Cereal Product Containing β-Glucan, Inulin and Plant Sterol

| Ingredients | |
|---|---|
| 54 g | water |
| 6 g | fibre enriched oat bran (containing 0.6 g β-glucan) |
| 30 g | berry jam (containing sugar, cowberry, blueberry, strawberry, raspberry, pectin, flavor) |
| 2 g | plant sterol fatty acid ester |
| 5 g | inulin |
| 3 g | lecithin |

The mixture of water and oat bran was fermented using Lactobacillus and a bifidobacteria culture. The sterol was mixed with the lecithin and all ingredients were worked together.

The product contained plant sterol 1.2%, β-glucan 0.6% and inulin 5%. The weight ratio between plant sterol and soluble fibre (β-glucan and inulin) was 1:4.6 (i.e. 0.2) and the ratio of inulin to insoluble fibre (β-glucan and inulin) was 1:1.12 (i.e. 0.89).

The invention claimed is:

1. A food product for lowering serum total and/or LDL cholesterol levels comprising at least one nutritional ingredient, dietary fibre and a plant sterol capable of achieving a cholesterol lowering effect, said dietary fibre and said plant sterol both being present in a higher amount than the one naturally occurring in the nutritional ingredient(s),
    wherein the dietary fibre comprises β-glucan,
    wherein the weight ratio in the food product of plant sterol, calculated as sterol equivalents, to β-glucan is 1 to 2-5, and
    wherein the dietary fibre further comprises psyllium.

2. A food product for lowering serum total and/or LDL cholesterol levels comprising at least one nutritional ingredient, dietary fibre and a plant sterol capable of achieving a cholesterol lowering effect, said dietary fibre and said plant sterol both being present in a higher amount than the one naturally occurring in the nutritional ingredient(s),
    wherein the dietary fibre comprises β-glucan,
    wherein the weight ratio in the food product of plant sterol, calculated as sterol equivalents, to β-glucan is 1 to 2-5, and
    wherein the dietary fibre further comprises inulin.

3. A food product for lowering serum total and/or LDL cholesterol levels comprising at least one nutritional ingredient, dietary fibre and a plant sterol capable of achieving a cholesterol lowering effect, said dietary fibre and said plant sterol both being present in a higher amount than the one naturally occurring in the nutritional ingredient(s),
    wherein the dietary fibre comprises β-glucan,
    wherein the weight ratio in the food product of plant sterol, calculated as sterol equivalents, to β-glucan is 1 to 2-5,
    wherein the plant sterol is selected from the group consisting of free sterols, free stanols, esterified sterols, esterified stanols and mixtures thereof, and
    wherein the esterified sterols comprise sterol fatty acid esters, and the esterified stanols comprise stanol fatty acid esters.

4. A food product for lowering serum total and/or LDL cholesterol levels comprising at least one nutritional ingredient, dietary fibre and a plant sterol capable of achieving a cholesterol lowering effect, said dietary fibre and said plant sterol both being present in a higher amount than the one naturally occurring in the nutritional ingredient(s),
    wherein the dietary fibre comprises β-glucan,
    wherein the weight ratio in the food product of plant sterol, calculated as sterol equivalents, to β-glucan is 1 to 2-5,
    wherein the food product comprises 0.1 to 25 g dietary fibre and 0.05 to 12.5 g plant sterol per 100 g food product,
    and wherein the dietary fibre and the plant sterol are present in a total amount being less than the amount of the individual dietary fibre or plant sterol required in a daily diet for obtaining the same reduction in serum total and/or LDL levels.

5. A food product for lowering serum total and/or LDL cholesterol levels comprising at least one nutritional ingredient, dietary fibre and a plant sterol capable of achieving a cholesterol lowering effect, said dietary fibre and said plant sterol both being present in a higher amount than the one naturally occurring in the nutritional ingredient(s),
    wherein the dietary fibre comprises β-glucan, wherein the weight ratio in the food product of plant sterol, calculated as sterol equivalents, to β-glucan is 1 to 2-5, and wherein the amounts of the dietary fibre and plant sterol are such that the dietary fibre is consumed at a rate of 1 g to 10 g per day and the plant sterol is consumed at a rate from 0.4 g to 5 g per day.

6. A food product for lowering serum total and/or LDL cholesterol levels comprising at least one nutritional ingredient, dietary fibre and a plant sterol capable of achieving a cholesterol lowering effect, said dietary fibre and said plant sterol both being present in a higher amount than the one naturally occurring in the nutritional ingredient(s), wherein the dietary fibre comprises β-glucan, wherein the weight ratio in the food product of plant sterol, calculated as sterol equivalents, to β-glucan is 1 to 2-5, and wherein the food product comprises a beverage.

7. The food product according to claim 6, wherein the amount of β-glucan is 0.1-5% and the amount of the plant sterol is 0.05-4% based on the weight of the food product.

8. A food product for lowering serum total and/or LDL cholesterol levels comprising at least one nutritional ingredient, dietary fibre and a plant sterol capable of achieving a cholesterol lowering effect, said dietary fibre and said plant sterol both being present in a higher amount than the one naturally occurring in the nutritional ingredient(s), wherein the dietary fibre comprises β-glucan, wherein the weight ratio in the food product of plant sterol, calculated as sterol equivalents, to β-glucan is 1 to 2-5, and wherein the food product comprises a fresh bakery product.

9. The food product according to claim 8, wherein the amount of β-glucan is 0.9-16% and the amount of the plant sterol is 0.3-8% based on the weight of the food product.

10. A food product for lowering serum total and/or LDL cholesterol levels comprising at least one nutritional ingredient, dietary fibre and a plant sterol capable of achieving a cholesterol lowering effect, said dietary fibre and said plant sterol both being present in a higher amount than the one naturally occurring in the nutritional ingredient(s), wherein the dietary fibre comprises β-glucan, wherein the weight ratio in the food product of plant sterol, calculated as sterol equivalents, to β-glucan is 1 to 2-5, and wherein the food product comprises a dry bakery product.

11. The food product according to claim 10, wherein the amount of β-glucan is 1.0-20% and the amount of the plant sterol is 0.5-10% based on the weight of the food product.

12. A food product for lowering serum total and/or LDL cholesterol levels comprising at least one nutritional ingredient, dietary fibre and a plant sterol capable of achieving a cholesterol lowering effect, said dietary fibre and said plant sterol both being present in a higher amount than the one naturally occurring in the nutritional ingredient(s), wherein the dietary fibre comprises β-glucan, wherein the weight ratio in the food product of plant sterol, calculated as sterol equivalents, to β-glucan is 1 to 2-5, and wherein the food product comprises a cereal product.

13. The food product according to claim 12, wherein the amount of β-glucan is 0.8-20% and the amount of the plant sterol is 0.4-10% based on the weight of the food product.

14. A food product for lowering serum total and/or LDL cholesterol levels comprising at least one nutritional ingredient, dietary fibre and a plant sterol capable of achieving a cholesterol lowering effect, said dietary fibre and said plant sterol both being present in a higher amount than the one naturally occurring in the nutritional ingredient(s), wherein the dietary fibre comprises β-glucan, wherein the weight ratio in the food product of plant sterol, calculated as sterol equivalents, to β-glucan is 1 to 2-5, wherein the food product comprises a bran product, and wherein the amount of β-glucan is 4%-25% and the amount of the plant sterol is 0.8-12.5% based on the weight of the food product.

15. A food product for lowering serum total and/or LDL cholesterol levels comprising at least one nutritional ingredient, dietary fibre and a plant sterol capable of achieving a cholesterol lowering effect, said dietary fibre and said plant sterol both being present in a higher amount than the one naturally occurring in the nutritional ingredient(s), wherein the dietary fibre comprises β-glucan, wherein the weight ratio in the food product of plant sterol, calculated as sterol equivalents, to β-glucan is 1 to 2-5, and wherein the food product comprises a dairy product.

16. The food product according to claim 15, wherein the amount of β-glucan is 0.1-20% and the amount of the plant sterol is 0.05-10% based on the weight of the food product.

17. A food product for lowering serum total and/or LDL cholesterol levels comprising at least one nutritional ingredient, dietary fibre and a plant sterol capable of achieving a cholesterol lowering effect, said dietary fibre and said plant sterol both being present in a higher amount than the one naturally occurring in the nutritional ingredient(s), wherein the dietary fibre comprises β-glucan, wherein the weight ratio in the food product of plant sterol, calculated as sterol equivalents, to β-glucan is 1 to 2-5, and wherein the food product comprises a vegetable oil based product.

18. The food product according to claim 17, wherein the amount of β-glucan is 0.6-16% and the amount of the plant sterol is 0.2-8% based on the weight of the food product.

19. A food product for lowering serum total and/or LDL cholesterol levels comprising at least one nutritional ingredient, dietary fibre and a plant sterol capable of achieving a cholesterol lowering effect, said dietary fibre and said plant sterol both being present in a higher amount than the one naturally occurring in the nutritional ingredient(s), wherein the dietary fibre comprises β-glucan, wherein the weight ratio in the food product of plant sterol, calculated as sterol equivalents, to β-glucan is 1 to 2-5, and wherein the food product comprises a sausage or meatball.

20. The food product according to claim 19, wherein the amount of β-glucan is 0.1-16% and the amount of the plant sterol is 0.05-8% based on the weight of the food product.

21. A food product for lowering serum total and/or LDL cholesterol levels comprising at least one nutritional ingredient, dietary fibre and a plant sterol capable of achieving a cholesterol lowering effect, said dietary fibre and said plant sterol both being present in a higher amount than the one naturally occurring in the nutritional ingredient(s), wherein the dietary fibre comprises β-glucan, wherein the weight ratio in the food product of plant sterol, calculated as sterol equivalents, to β-glucan is 1 to 2-5, and wherein the food product comprises a ready mix.

22. The food product according to claim 21, wherein the amount of β-glucan is 0.1-20% and the amount of the plant sterol is 0.05-10% based on the weight of the food product.

23. The food product according to claim 5, wherein the amounts of the dietary fibre and plant sterol are such that the dietary fibre is consumed at a rate of 2 g to 5 g per day.

24. The food product according to claim 5, wherein the amounts of the dietary fibre and plant sterol are such that the plant sterol is consumed at a rate from 0.8 g to 2 g per day.

25. The food product according to claim 7, wherein the amount of β-glucan is 0.5-1% based on the weight of the food product.

26. The food product according to claim 7, wherein the amount of the plant sterol is 0.2-1.5% based on the weight of the food product.

27. The food product according to claim 9, wherein the amount of β-glucan is 2.4-10% based on the weight of the food product.

28. The food product according to claim 27, wherein the amount of β-glucan is 3-5% based on the weight of the food product.

29. The food product according to claim 9, wherein the amount of the plant sterol is 0.8-5% based on the weight of the food product.

30. The food product according to claim 29, wherein the amount of the plant sterol is 1-4% based on the weight of the food product.

31. The food product according to claim 11, wherein the amount of β-glucan is 3.2-15% based on the weight of the food product.

32. The food product according to claim 31, wherein the amount of β-glucan is 4.4-10% based on the weight of the food product.

33. The food product according to claim 11, wherein the amount of the plant sterol is 1.6-7.5% based on the weight of the food product.

34. The food product according to claim 33, wherein the amount of the plant sterol is 2.2-5% based on the weight of the food product.

35. The food product according to claim 13, wherein the amount of β-glucan is 1.6-16%.

36. The food product according to claim 13, wherein the amount of the plant sterol is 0.8-8% based on the weight of the food product.

37. The food product according to claim 14, wherein the amount of β-glucan is 6-20%.

38. The food product according to claim 14, wherein the amount of the plant sterol is 1.2-10% based on the weight of the food product.

39. A food product for lowering serum total and/or LDL cholesterol levels comprising at least one nutritional ingredient, dietary fibre and a plant sterol capable of achieving a cholesterol lowering effect, said dietary fibre and said plant sterol both being present in a higher amount than the one naturally occurring in the nutritional ingredient(s), wherein the dietary fibre comprises β-glucan, wherein the weight ratio in the food product of plant sterol, calculated as sterol equivalents, to β-glucan is 1 to 2-5, and wherein the food product comprises a non-dairy product.

40. The food product according to claim 16, wherein the amount of β-glucan is 0.8-8% based on the weight of the food product.

41. The food product according to claim 16, wherein the amount of the plant sterol is 0.4-4% based on the weight of the food product.

42. The food product according to claim 18, wherein the amount of β-glucan is 2.6-10% based on the weight of the food product.

43. The food product according to claim 18, wherein the amount of the plant sterol is 1.3-5% based on the weight of the food product.

44. The food product according to claim 20, wherein the amount of β-glucan is 0.2-5% based on the weight of the food product.

45. The food product according to claim 20, wherein the amount of the plant sterol is 0.1-2.5% based on the weight of the food product.

46. The food product according to claim 22, wherein the amount of β-glucan is 1-10% based on the weight of the food product.

47. The food product according to claim 22, wherein the amount of the plant sterol is 0.5-5% based on the weight of the food product.

48. The food product according to claim 7, wherein the amount of β-glucan is 0.5-1% and the amount of the plant sterol is 0.2-1.5% based on the weight of the food product.

49. The food product according to claim 9, wherein the amount of β-glucan is 3-5% and the amount of the plant sterol is 1-4% based on the weight of the food product.

50. The food product according to claim 11, wherein the amount of β-glucan is 4.4-10% and the amount of the plant sterol is 2.2-5% based on the weight of the food product.

51. The food product according to claim 13, wherein the amount of β-glucan is 1.6-16% and the amount of the plant sterol is 0.8-8% based on the weight of the food product.

52. The food product according to claim 14, wherein the amount of β-glucan is 6-20% and the amount of the plant sterol is 1.2-10% based on the weight of the food product.

53. The food product according to claim 16, wherein the amount of β-glucan is 0.8-8% and the amount of the plant sterol is 0.4-4% based on the weight of the food product.

54. The food product according to claim 18, wherein the amount of β-glucan is 2.6-10% and the amount of the plant sterol is 1.3-5% based on the weight of the food product.

55. The food product according to claim 20, wherein the amount of β-glucan is 0.2-5% and the amount of the plant sterol is 0.1-2.5% based on the weight of the food product.

56. The food product according to claim 22, wherein the amount of β-glucan is 1-10% and the amount of the plant sterol is 0.5-5% based on the weight of the food product.

* * * * *